US011399989B2

United States Patent
Polidori et al.

(10) Patent No.: US 11,399,989 B2
(45) Date of Patent: Aug. 2, 2022

(54) METHOD AND APPARATUS FOR MANUFACTURING ABSORBENT SANITARY PRODUCTS AND AN ABSORBENT SANITARY PRODUCT

(71) Applicant: Fameccanica.Data S.p.A., Pescara (IT)

(72) Inventors: Domenico Polidori, Pescara (IT); Diego Gualtieri, Pescara (IT); Gabriele Sablone, Montesilvano (IT)

(73) Assignee: Fameccanica Data S.p.A.

( * ) Notice: Subject to any disclaimer, the term of this patent is extended or adjusted under 35 U.S.C. 154(b) by 598 days.

(21) Appl. No.: 15/077,325

(22) Filed: Mar. 22, 2016

(65) Prior Publication Data

US 2016/0331600 A1 Nov. 17, 2016

(51) Int. Cl.
*A61F 13/15* (2006.01)
*A61F 13/49* (2006.01)
(Continued)

(52) U.S. Cl.
CPC .. *A61F 13/49011* (2013.01); *A61F 13/15593* (2013.01); *A61F 13/15699* (2013.01);
(Continued)

(58) Field of Classification Search
CPC ............ A61F 13/49011; A61F 13/4902; A61F 13/49061; A61F 13/15699;
(Continued)

(56) References Cited

U.S. PATENT DOCUMENTS

| 4,081,301 A | * | 3/1978 | Buell | ................ | A61F 13/15593 |
| | | | | | 156/164 |
| 6,291,039 B1 | * | 9/2001 | Combe | ................ | A41D 27/245 |
| | | | | | 428/35.2 |

(Continued)

FOREIGN PATENT DOCUMENTS

| EP | 1876275 | | 1/2008 |
| EP | 2186493 | † | 5/2010 |

(Continued)

OTHER PUBLICATIONS

Italian Search Report and Written Opinion dated Nov. 5, 2015 for Application No. 102015000014817.

(Continued)

*Primary Examiner* — Jeffry H Aftergut
(74) *Attorney, Agent, or Firm* — Eversheds Sutherland (US) LLP (57) ABSTRACT

A method for manufacturing absorbent sanitary products, comprising the steps of: forming a first and a second continuous elastic band, which are movable parallel to each other in a machine direction, fixing a plurality of absorbent panels between said first and second continuous elastic bands, arranged in a direction transverse to the machine direction, and spaced apart in said machine direction, wherein each of said elastic bands is formed by means of a method comprising the steps of: continuously feeding a plurality of tensioned elastic threads (30) in said machine direction, continuously feeding a pair of non-elastic webs arranged on opposite sides of said plurality of elastic
(Continued)

threads, welding said pair of non-elastic webs to each other by means of a welding pattern comprising anchoring welds and/or containing and guiding welds.

8 Claims, 4 Drawing Sheets (51) Int. Cl.
*B29C 65/00* (2006.01)
*B29C 65/08* (2006.01)
B29C 65/74 (2006.01)
A61F 13/496 (2006.01)
B29D 99/00 (2010.01)
B29L 31/48 (2006.01)

(52) U.S. Cl.
CPC .. *A61F 13/15739* (2013.01); *A61F 13/15747* (2013.01); *A61F 13/4902* (2013.01); *A61F 13/49061* (2013.01); *B29C 65/086* (2013.01); *B29C 66/1122* (2013.01); *B29C 66/21* (2013.01); *B29C 66/433* (2013.01); *B29C 66/7294* (2013.01); *B29C 66/81433* (2013.01); *B29C 66/81469* (2013.01); *B29C 66/83411* (2013.01); *B29C 66/8432* (2013.01); *A61F 13/496* (2013.01); *A61F 2013/15861* (2013.01); *A61F 2013/49025* (2013.01); *A61F 2013/49026* (2013.01); *A61F 2013/49036* (2013.01); *A61F 2013/49092* (2013.01); *B29C 65/7443* (2013.01); *B29D 99/0064* (2013.01); *B29K 2995/0046* (2013.01); *B29L 2031/4878* (2013.01)

(58) Field of Classification Search
CPC .......... A61F 13/15747; A61F 13/15593; A61F 13/15739; A61F 2013/49026; A61F 2013/49036; A61F 13/496; A61F 2013/15861; A61F 2013/49025; A61F 2013/49092; A61F 13/15577; A61F 13/15764; A61F 13/49017; A61F 2013/15121; A61F 2013/15146; A61F 2013/15869; B29C 66/83411; B29C 65/086; B29C 66/8432; B29C 66/433; B29C 66/81433; B29C 66/21; B29C 66/7294; B29C 66/1122; B29C 66/81469; B29C 65/7443; B29K 2995/0046; B29D 99/0064; B29L 2031/4878
See application file for complete search history.

(56) References Cited

U.S. PATENT DOCUMENTS

| 7,582,348 B2 † | 9/2009 | Ando |
| 8,940,116 B2 * | 1/2015 | Gilgenbach ....... A61F 13/15804 156/163 |
| 2006/0069373 A1 † | 3/2006 | Schlinz |
| 2006/0270302 A1 * | 11/2006 | Ando .................. A61F 13/4902 442/328 |
| 2009/0326504 A1 * | 12/2009 | Kaneda ............. A61F 13/49011 604/385.23 |
| 2010/0076394 A1 † | 3/2010 | Hayase |
| 2012/0095429 A1 * | 4/2012 | Kobayashi ........ A61F 13/15804 604/385.16 |
| 2013/0306226 A1 | 11/2013 | Zink et al. |
| 2016/0058624 A1 * | 3/2016 | Hohm ............... A61F 13/15593 428/198 |

FOREIGN PATENT DOCUMENTS

| WO | WO2009/067055 | † | 5/2009 |
| WO | WO-2009/067055 A1 | * | 5/2009 |
| WO | 2010126415 | | 11/2010 |
| WO | 2014156949 A | | 10/2014 |

OTHER PUBLICATIONS

Office Action and Search Report in related application CN201610298799.6 dated Apr. 24, 2019.
Summons to attend oral proceedings in related application EP16159313.2, dated Mar. 26, 2019.

* cited by examiner
† cited by third party

METHOD AND APPARATUS FOR MANUFACTURING ABSORBENT SANITARY PRODUCTS AND AN ABSORBENT SANITARY PRODUCT

CROSS-REFERENCE TO RELATED APPLICATIONS

This application claims benefit of Italian patent application number 102015000014817, filed May 12, 2015, which is herein incorporated by reference.

BACKGROUND OF THE INVENTION

Field of the Invention

The present invention relates to a method and an apparatus for manufacturing absorbent sanitary products. The invention also relates to an absorbent sanitary product.

The invention has been developed with particular regard to the manufacture of pant-type absorbent sanitary products, commonly known as training pants. As is widely known, training pants can be pre-closed, i.e. with permanently closed waist-bands, or openable and reclosable, in which the corresponding lateral edges of the waist-bands are fixed to each other by means of reclosable closing elements.

The invention is, however, not limited to this specific product and can be equally used for manufacturing other types of absorbent sanitary products, such as diapers for incontinent adults.

Description of Prior Art

The technique generally used to produce pre-closed pant-type absorbent sanitary products includes forming a first and a second continuous elastic band, which are movable parallel to each other in a machine direction, wherein each continuous elastic band comprises a plurality of tensioned elastic threads parallel to one another, arranged between two non-elastic webs fixed to each other. A plurality of absorbent panels arranged in a direction transverse to the machine direction are fastened between the first and the second continuous elastic bands, at positions spaced apart from each other in the machine direction. Then, the two continuous elastic bands are overlapped and welded to each other in the transverse direction at intermediate positions between the absorbent panels. Together with the welding, a transverse cut of the elastic bands is carried out to form individual absorbent sanitary products.

Each absorbent sanitary product obtained in this manner has a front waist-band and a back waist-band joined together by welds arranged on the sides, and an absorbent panel that extends through the user's groin region, with opposite ends fixed to the front waist-band and to the rear waist-band.

One example of a method for manufacturing absorbent sanitary products of this type is described in EP-A-2186493. The method described in this document involves the gluing of elastic elements under tension to non-elastic webs fed continuously in a machine direction to form front and rear waist-bands of the absorbent sanitary products, and the gluing, at regular intervals, of the absorbent panels transversely arranged between the elastic bands. The absorbent panels are provided with elastic elements for the legs, which are also fixed to the absorbent panel by glue.

The method according to EP-A-2186493 uses considerable amounts of glue. The use of glue for bonding the elastic elements to the corresponding webs involves various problems, including the difficulty of ensuring the dispensing of constant quantities of glue, the possibility of clogging of the glue-dispensing apparatuses, and the risk of contamination of parts of the plant etc.

During the manufacture of elastic structures of an absorbent sanitary product, it is often necessary to include sections in which the elastic elements are anchored to respective webs and sections in which the elastic elements are free to move in the longitudinal direction with respect to the respective webs. With the technology that provides for the fixing of the elastic elements to the webs by means of glue, the formation of anchoring areas of the intermittent elastic elements is obtained by the intermittent dispensing of glue, by means of solenoid valves piloted by a control unit. This technique involves an uncontrollable time delay and the impossibility of forming anchoring areas spaced apart by intervals of less than a minimum size, which depends on the delay time of the solenoid valves and the production line speed.

To overcome the problems arising from the use of glue for bonding elastic elements to respective webs, it has been previously proposed to bond elastic elements within tubular sleeves by means of welding. The document U.S. Pat. No. 6,291,039 describes an elastic structure comprising a tubular sleeve and at least one elastic thread, which extends within the sleeve in a longitudinal direction. The elastic thread is tensioned in the longitudinal direction and is anchored to the tubular sleeve by means of a plurality of connecting portions spaced apart from each other in the longitudinal direction. Each connecting portion comprises two welds, which weld together opposite layers of the tubular sleeve. The two welds of each connecting portion have respective proximal surfaces facing towards the elastic thread, spaced apart by a distance less than the diameter of the non-tensioned thread. When the longitudinal tension of the thread ceases, the elastic thread expands radially and remains anchored by interference with the welds forming the connecting portions. These welds are formed by means of a thermal or ultrasonic welding device comprising two cooperating wheels, one of which is provided on its periphery with projections spaced apart in a circumferential direction and provided with respective notches through which the tensioned thread is passed.

This solution is difficult to use when elastic structures must be produced with elasticized portions alternating with non-elasticized portions. One known solution envisages the cyclical moving apart of the welding wheels in order to interrupt the welding in the non-elasticized portions. The welding wheels must be moved radially relative to each other with a high frequency, up to 1000 times per minute. A process of intermittent welding of this type generates vibrations that produce a decline in quality of the weld, particularly serious in the case of ultrasonic welding. Furthermore, in the sections where the webs are not welded to each other, the elastic elements are not retained radially with respect to the webs, and in these areas the webs are detached from each other and form loose areas with lower resistance, which worsen the quality of the product perceived by users.

SUMMARY OF THE INVENTION

The present invention aims to provide a method and apparatus for manufacturing absorbent sanitary products and a relative absorbent sanitary product, which overcome the problems of the prior art.

According to the present invention, this object is achieved by a method, by an apparatus and by an absorbent sanitary product having the characteristics forming the subject of the attached claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

DETAILED DESCRIPTION

Figure 1:
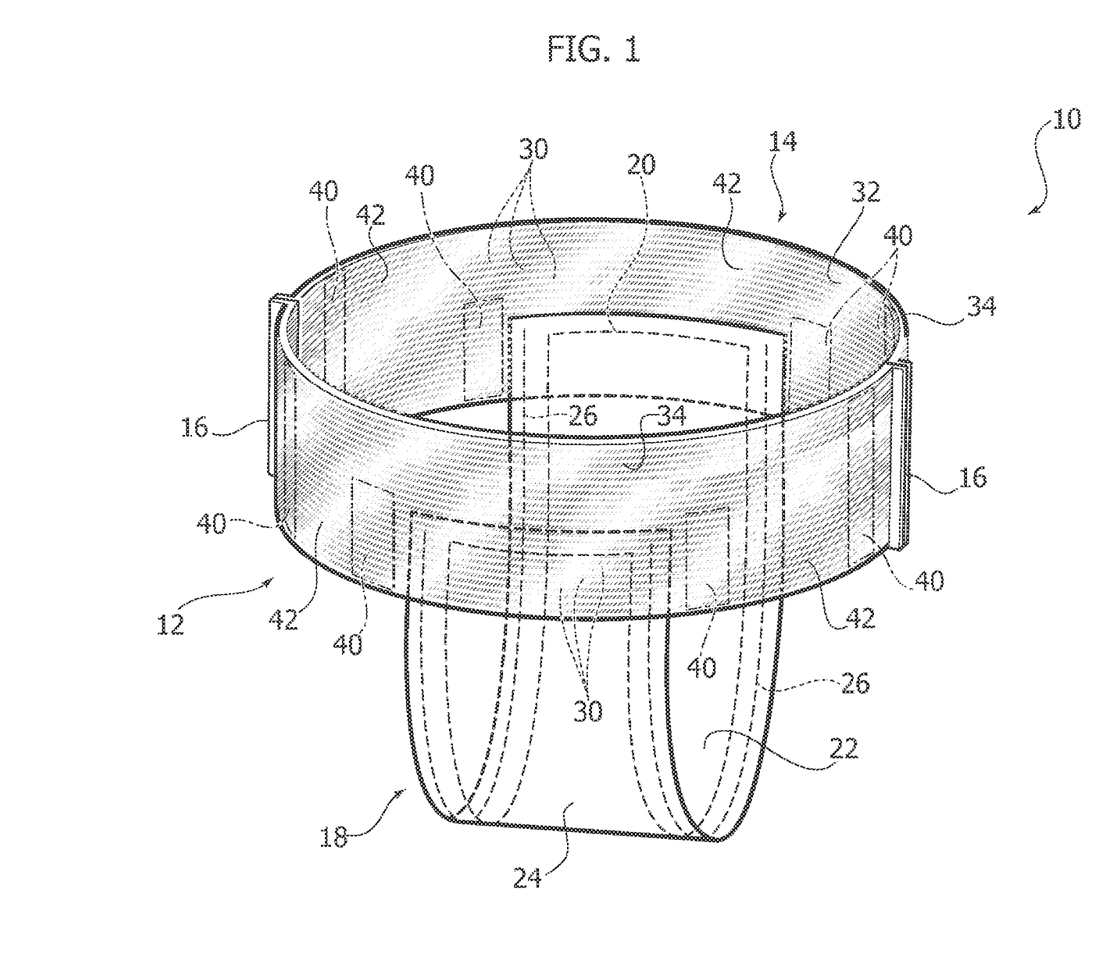
FIG. 1 is a schematic perspective view of an absorbent sanitary article according to the present invention.
Figures 2, 3:
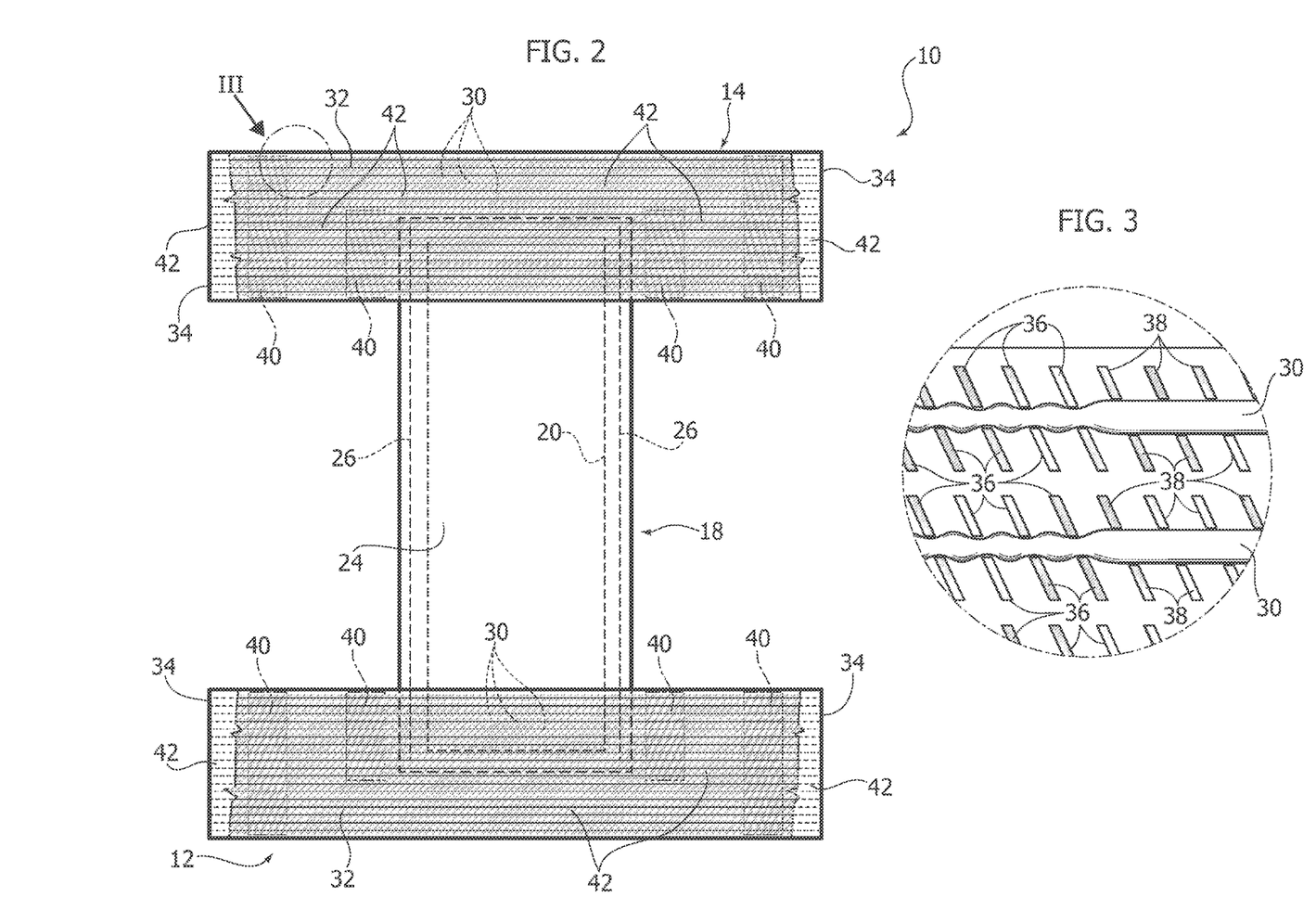
FIG. 2 is a schematic view of the absorbent sanitary product of FIG. 1 in an open configuration.
FIG. 3 is an enlarged schematic view of the detail indicated by the arrow Ill in FIG. 2.

With reference to FIGS. 1 and 2, numeral 10 indicates an absorbent sanitary product according to the present invention. The product 10 depicted in FIG. 1 is a pre-closed pant-diaper comprising a front waist-band 12 and a back waist-band 14. The two waist-bands 12, 14 can be two separate tapes or can be lateral regions of a single web.

In the illustrated embodiment, the waist-bands 12, 14 are joined together by welds 16 that, during use, are located along the user's hips. The invention also applies to the case of pant-diapers of the openable and closable type, in which there is no welding along the side edges of the waist-bands 12, 14 and these waist-bands are equipped with openable and reclosable closing elements. In the following description, reference will only be made to the pre-closed pant-diapers, but it is understood that the above description also equally applies to openable and reclosable absorbent sanitary products.

The product 10 comprises an absorbent panel 18 having opposite ends fixed to the front waist-band 12 and to the back waist-band 14, respectively. The absorbent panel 18 comprises an absorbent core 20 usually formed from cellulose fluff and super-absorbent powders. The absorbent panel 18 comprises a liquid-permeable topsheet 22 and a liquid-impermeable backsheet 24, which enclose the absorbent core 20 in a sandwich manner. The absorbent panel 18 further comprises elastic elements for the legs 26, which can be formed by elastic threads enclosed between the topsheet 22 and the backsheet 24, or from barrier leg cuffs applied on the topsheet 22.

Each of the two waist-bands 12, 14 is an elasticized composite structure comprising a plurality of elastic threads 30 parallel to each other, for example, Lycra®, enclosed between an inner web 32 and an outer web 34 of flexible non-elastic material, for example non-woven fabric.

According to the present invention, the elastic threads 30 are anchored to the inner web 32 and to the outer web 34 of the respective waist-band 12, 14, without glue, by means of welds that fix the inner web 32 and the outer web 34 together.

The inner web 32 and the outer web 34 of each waist-band 12, 14 are welded together by a welding pattern evenly distributed along the entire surface of the waist-bands 12, 14. With reference to FIG. 3, the welding pattern comprises anchoring welds 36 and containing and guiding welds 38. In the illustrated example, the anchoring welds 36 and the containing and guiding welds 38 are arranged in pairs. The pairs of anchoring welds 36 and pairs of containing and guiding welds 38 are spaced apart in the direction of the longitudinal axis of the elastic threads 30. Each pair has two welds 36, 38 arranged on opposite sides of a respective elastic thread 30. When the welds 36, 38 between the webs 32, 34 are being carried out, the elastic threads 30 are in a tensioned state. The elastic threads 30 in a tensioned state have a diameter less than the resting diameter. The anchoring welds 36 of each pair have respective proximal surfaces facing the respective elastic thread 30, which are spaced apart in a direction orthogonal to the longitudinal axis of the elastic thread 30 by a distance less than the diameter of the respective non-tensioned elastic thread 30. The containing and guiding welds 38 of each pair have respective proximal surfaces facing the respective elastic thread 30, which are spaced apart in a direction orthogonal to the longitudinal axis of the elastic thread 30 by a distance equal to or greater than the diameter of the non-tensioned thread 30.

When the tension of the elastic threads 30 is released, the elastic threads 30 expand in a radial direction with respect to the tensioned state. At the anchoring welds 36, the elastic threads 30 are compressed radially between the proximal surfaces of the pairs of anchoring welds 36. In the space between the pairs of anchoring welds 36, the elastic threads 30 form bulges. At the containing and guiding welds 38, the elastic threads 30 are free to expand to their non-tensioned diameter. At the containing and guiding welds 38, the elastic threads 30 are free to move axially with respect to the containing and guiding welds 38. The containing and guiding welds 38 retain the respective elastic threads 30 with respect to the webs 32, 34 in the radial direction with respect to the longitudinal axis of the elastic threads 30. The webs 32, 34 are welded together in a continuous and uniform manner along the entire surface of the waist-bands 12, 14.

With reference to FIGS. 1 and 2, on the surfaces of the waist-bands 12, 14, anchoring areas 40 are identifiable in which the webs 32, 34 are fixed to each other by means of anchoring welds 36 and containing and guiding areas 42 in which the webs 32, 34 are fixed together by means of containing and guiding welds 38. The anchoring areas 40 and the containing and guiding areas 42 can be arranged in various ways on the surface of the waist-bands 12, 14. FIGS. 1 and 2 show an exemplary arrangement in which the anchoring areas 40 are located in the end areas of the waist-bands 12, 14, adjacent to the welds 16 and in areas adjacent to the side edges of the absorbent panel 18 and all the other areas of the waist-bands 12, 14 are containing and guiding areas 42. It is understood of course that this is not binding and can be varied according to necessity.

Preferably, the elastic elements for the legs 26 are fixed to the topsheet 22 and to the backsheet 24 or to the barrier elements for the legs using a glue-free technology, similar to that described previously, with anchoring welds alternating with containing and guiding welds. Preferably, the crotch area of the absorbent panel 18 is provided with anchoring welds for the elastic elements for the legs 26, while the end areas of the elastic elements for the legs 26 are fixed to the topsheet 22 and to the backsheet 24 or to the barrier elements for the legs by means of containing and guiding welds.

Figure 4:
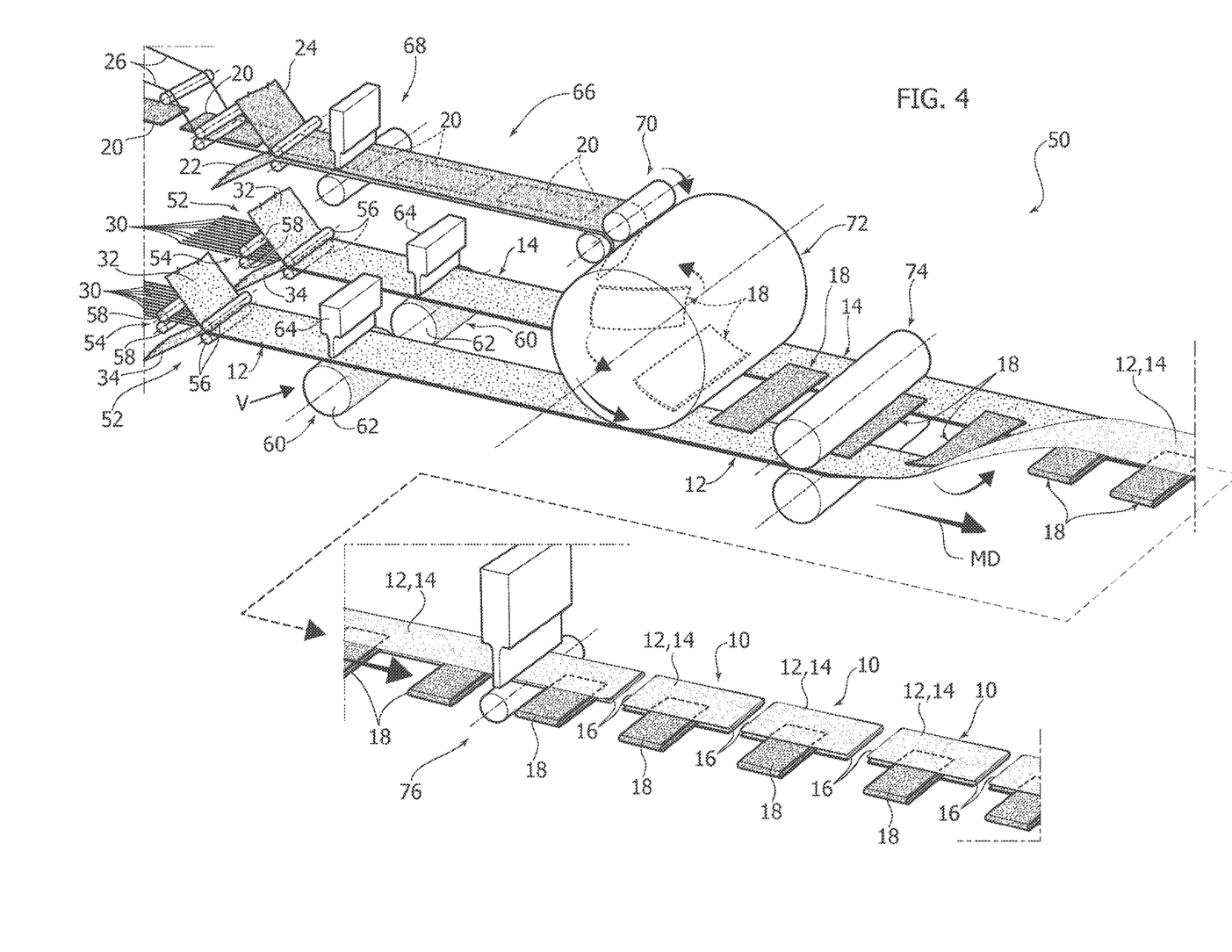
FIG. 4 is a schematic perspective view illustrating the method and the apparatus according to the present invention.

In FIG. 4, an apparatus for manufacturing absorbent sanitary products of the type previously described is schematically indicated by 50. The elements corresponding to those previously described are indicated with the same reference numerals.

The apparatus 10 comprises two elastic band-forming units 52, for forming the two continuous elastic bands 12, 14, which are movable in a machine direction MD. Each forming unit 52 comprises a feeding device 54, configured to advance a plurality of continuous parallel elastic threads 30 in the machine direction MD, in a tensioned state. The feeding device 54 comprises a pair of downstream rollers 56 and a pair of upstream rollers 58. The pairs of rollers 56, 58 are controlled, during operation, with different peripheral speeds from each other. The peripheral speed of the pair of downstream rollers 56 is higher than the peripheral speed of the pair of upstream rollers 58, so that the elastic threads 30 are elastically stretched with a stretching ratio equal to the ratio between the peripheral speeds of the pairs of rollers 56, 58. Two continuous webs of non-woven fabric 32, 34 are fed to the pair of downstream rollers 56 on opposite sides of the tensioned elastic threads 30.

Each elastic band-forming unit 52 comprises a welding assembly 60 arranged downstream of the respective feeding device 54. The welding assembly 60 is preferably an ultrasonic welding assembly and comprises an anvil wheel 62 and a stationary sonotrode 64. Each welding assembly 60 welds together the webs 32, 34 of each continuous elastic band 12, 14 with a welding pattern that includes anchoring welds 36 and containing and guiding welds 38 arranged around the tensioned elastic threads 30, as previously described.

The apparatus 50 comprises an absorbent panel-forming unit 66, for forming absorbent panels 18. The unit 66 forms a continuous chain of absorbent cores 20 that are made to advance in a second machine direction. A continuous web of topsheets 22 and a continuous web of backsheets 24 are fed from opposite sides of the continuous chain of absorbent cores 20. Elastic elements for the legs 26 are fed between the topsheet 22 and the backsheet 24. Alternatively, the elastic elements for the legs 26 can be enclosed in respective tubular sleeves of non-woven fabric, forming barrier leg cuffs applied on the topsheet 22. The unit 66 comprises a second welding assembly 68 configured to form a welding pattern around the elastic elements for the legs 26, which comprises anchoring welds alternating with containing and guiding welds. The second welding assembly 68 is functionally analogous to the welding assemblies 60 that form the welding pattern on the elastic bands 12, 14. The elastic elements for the legs 26 may be arranged between the topsheet 22 and the backsheet 24, or they can be arranged within tubular sleeves forming barrier elements for the legs.

A cutting assembly 70 is arranged downstream of the welding assembly 68, which performs the transverse cut of the topsheet 22 and of the backsheet 24 at intermediate positions between the absorbent cores 20, in order to form individual absorbent panels 18. Downstream of the cutting assembly 70, the individual absorbent panels 18 are picked up by a turn and repitch unit 72, which rotates the individual absorbent panels 18 by 90° with respect to the machine direction and arranges them at a relative predetermined pitch. The turn and repitch unit 72 applies the absorbent panels 18 at a predetermined pitch on the two continuous elastic bands 12, 14, which advance in the machine direction MD.

Downstream of the turn and repitch unit 72, a continuous chain of blanks of absorbent sanitary products is formed with respective absorbent panels 18 arranged transversely to the machine direction MD. The continuous chain of product blanks is passed through a fastening unit 74, which fixes the absorbent panels 18 to the two continuous elastic bands 12, 14. Preferably, the fixing of the absorbent panels 18 to the two continuous elastic bands 12, 14 is carried out by welding. Subsequently, a longitudinal folding device folds the continuous chain of product blanks along a central longitudinal axis, so as to overlap the continuous elastic bands 12, 14 and, at the same time, fold the absorbent panels 18 along a central longitudinal axis. Subsequently, a cutting and welding unit 76 carries out the transverse welds 16, which join together the elastic bands 12, 14, and cuts the bands 12, 14 in the transverse direction, between two welding lines 16 adjacent to each other, so as to form individual absorbent sanitary products 10.

Figure 5:
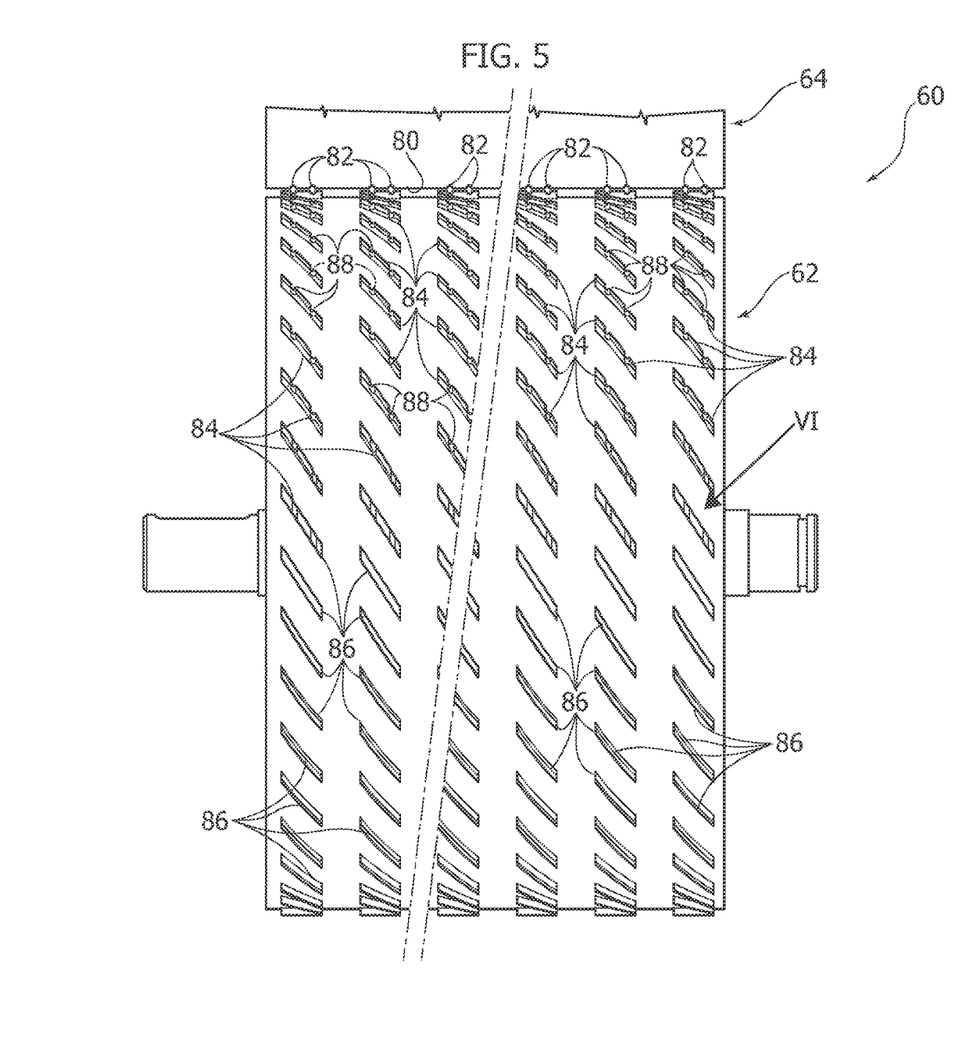
FIG. 5 is a front view of the welding apparatus indicated by the arrow V in FIG. 4.
Figure 6:
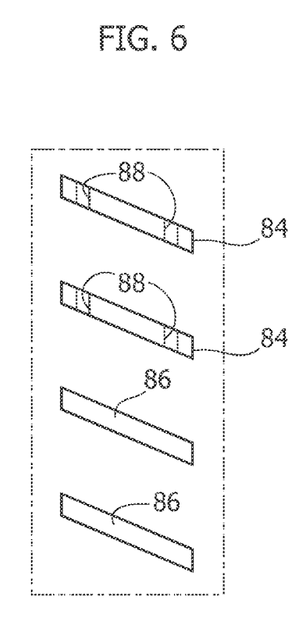
FIG. 6 is a detail on a larger scale of the part indicated by the arrow VI in FIG. 5.

FIG. 5 schematically illustrates an embodiment of a welding assembly 60 for forming the welding pattern, including anchoring welds 36 and containing and guiding welds 38, between the webs 32, 34 of each continuous elastic band 12, 14. The welding assembly 60 comprises a sonotrode 64 having a welding surface 80 facing an anvil wheel 62. A respective continuous elastic band (not shown in FIG. 5) is made to pass between the sonotrode 64 and the anvil wheel 62 with the elastic threads 30 in a tensioned state. The sonotrode 64 is provided with a plurality of grooves 82 on the welding surface 80, each of which receives a respective elastic thread 30. The grooves 82 have a width that is slightly larger than the diameter of the respective threads 30 in a tensioned state. The anvil wheel 62 has a plurality of circumferential arrays of teeth 84, 86. In each circumferential array, teeth 84 alternate with teeth 86. The teeth 84 have head surfaces provided with grooves 88 located alongside the respective grooves 82 of the sonotrode 64. The grooves 88 have a width that is larger than the diameter of the non-tensioned elastic threads 30. The teeth 86 have head surfaces without grooves. During operation, when the teeth 86 pass level with the sonotrode 64, they carry out anchoring welds 36 on the elastic bands 12, 14, spaced apart in the transverse direction by a distance slightly greater than the diameter of the tensioned elastic threads 30 and essentially less than the diameter of the non-tensioned elastic threads. When the teeth 84 pass level with the sonotrode 64, they carry out containing and guiding welds 38 on the elastic bands 12, 14, located on opposite sides of each elastic thread 30, and spaced apart in the transverse direction by a distance equal to or greater than the diameter of the non-tensioned elastic threads 30. The teeth 84, 86 are distributed on the circumference of the anvil wheel 62 so as to reproduce a required welding pattern with the required alternation between anchoring welds 36 and containing and guiding welds 38.

Of course, without prejudice to the principle of the invention, the details of construction and the embodiments can be widely varied with respect to those described and illustrated, without thereby departing from the scope of the invention as defined by the claims that follow.

The invention claimed is:

1. A method for manufacturing absorbent sanitary products, comprising the steps of:
    forming a first and a second continuous elastic band, which are movable parallel to each other in a machine direction;
    fixing a plurality of absorbent panels between said first and second continuous elastic bands, arranged in a direction transverse to the machine direction and spaced apart in said machine direction;

wherein each of said continuous elastic bands is formed by a method comprising the steps of:
continuously feeding a plurality of tensioned elastic threads in said machine direction,
continuously feeding a pair of non-elastic webs arranged on opposite sides of said plurality of elastic threads,
welding said pair of non-elastic webs to each other by pressing said pair of non-elastic webs against each other with an anvil wheel having a plurality of teeth, wherein the plurality of teeth comprise one or more first teeth having a smooth head surface and one or more second teeth having a grooved surface,
wherein pressing said pair of non-elastic webs against each other with the one or more first teeth produces anchoring welds, and pressing said pair of non-elastic webs against each other with the one or more second teeth produces guiding welds to form a welding pattern comprising anchoring welds and guiding welds,
wherein the anchoring welds comprise pairs of welds arranged on opposite sides of a respective elastic thread and spaced apart in the transverse direction by a distance greater than the diameter of the tensioned elastic thread but less than the diameter of the non-tensioned elastic thread, and
wherein the guiding welds comprise pairs of welds arranged on opposite sides of a respective elastic thread and spaced apart in the transverse direction by a distance equal to or greater than the diameter of the non-tensioned elastic thread.

2. A method according to claim 1, comprising the step of applying elastic elements for legs to said absorbent panels using a welding pattern, which comprises anchoring welds alternating with guiding welds,
wherein the anchoring welds comprise pairs of welds arranged on opposite sides of a respective elastic element and spaced apart by a distance greater than the elastic element under tension but less than the diameter of the non-tensioned elastic element, and
wherein the guiding welds comprise pairs of welds arranged on opposite sides of a respective elastic thread and spaced apart by a distance equal to or greater than the diameter of the non-tensioned elastic material.

3. A method according to claim 2 wherein the step of applying elastic elements for legs to said absorbent panels using a welding pattern is conducted such that said welding pattern comprises a plurality of pairs of alternating anchoring welds and guiding welds including at least one first pair of anchoring welds adjacent to and followed by at least one first pair of guiding welds followed by at least one second pair of anchoring welds adjacent to and followed by at least one second pair of guiding welds.

4. A method according to claim 1, further comprising the steps of:
overlapping said elastic bands on each other;
welding said elastic bands to each other in a transverse direction, at intermediate positions between said absorbent panels; and
transversally cutting said elastic bands.

5. A method according to claim 1 wherein the step of welding is conducted such that the welding pattern comprises a plurality of pairs of alternating anchoring welds and guiding welds including at least one first pair of anchoring welds adjacent to and followed by at least one first pair of guiding welds followed by at least one second pair of anchoring welds adjacent to and followed by at least one second pair of guiding welds.

6. A method according to claim 1 further comprising pressing said pair of non-elastic webs against each other with a stationary sonotrode configured to sonically weld said pair of non-elastic webs using the plurality of teeth.

7. A method for manufacturing absorbent sanitary products, comprising the steps of:
forming a first and a second continuous elastic band, which are movable parallel to each other in a machine direction;
fixing a plurality of absorbent panels between said first and second continuous elastic bands, arranged in a direction transverse to the machine direction and spaced apart in said machine direction;
wherein each of said continuous elastic bands is formed by a method comprising the steps of:
continuously feeding a plurality of tensioned elastic threads in said machine direction,
continuously feeding a pair of non-elastic webs arranged on opposite sides of said plurality of elastic threads,
welding said pair of non-elastic webs to each other by a welding pattern comprising anchoring welds and guiding welds,
wherein the anchoring welds comprise pairs of welds arranged on opposite sides of a respective elastic thread and spaced apart in the transverse direction by a distance greater than the diameter of the tensioned elastic thread but less than the diameter of the non-tensioned elastic thread, and
wherein the guiding welds comprise pairs of welds arranged on opposite sides of a respective elastic thread and spaced apart in the transverse direction by a distance equal to or greater than the diameter of the non-tensioned elastic thread, and
wherein the step of welding said pair of non-elastic webs to each other by a welding pattern comprising anchoring welds and guiding welds comprises ultrasonically welding said pair of non-elastic webs to each other using:
an anvil wheel comprising a plurality of circumferential arrays of teeth comprising:
a plurality of teeth each containing grooves each having a width that is larger than the diameter of the non-tensioned elastic threads configured to produce guiding welds, and
a plurality of teeth without grooves configured to produce anchoring welds; and
a stationary sonotrode comprising a welding surface and a plurality of grooves each configured to receive a respective elastic thread, each of the plurality of grooves having a width that is slightly larger than the diameter of the respective elastic thread in a tensioned state.

8. A method for manufacturing a continuous elastic band for absorbent sanitary products comprising the steps of:
continuously feeding a plurality of tensioned elastic threads in said machine direction,
continuously feeding a pair of non-elastic webs arranged on opposite sides of said plurality of elastic threads,
welding said pair of non-elastic webs to each other by pressing said pair of non-elastic webs against each other with an anvil wheel having a plurality of teeth, wherein the plurality of teeth comprise one or more first teeth having a smooth head surface and one or more second teeth having a grooved surface, wherein pressing said pair of non-elastic webs against each other with the one or more first teeth produces anchoring welds, and pressing said pair of non-elastic webs against each other with the one or more second teeth produces guiding welds to form a welding pattern comprising anchoring welds and guiding welds, wherein the anchoring welds comprise pairs of welds arranged on opposite sides of a respective elastic thread and spaced apart in the transverse direction by a distance greater than the diameter of the tensioned elastic thread but less than the diameter of the non-tensioned elastic thread, and wherein the guiding welds comprise pairs of welds arranged on opposite sides of a respective elastic thread and spaced apart in the transverse direction by a distance equal to or greater than the diameter of the non-tensioned elastic thread.

* * * * *